(12) United States Patent
Thompson et al.

(10) Patent No.: US 8,353,892 B2
(45) Date of Patent: Jan. 15, 2013

(54) DEVICES AND METHODS FOR CONTROLLED-DEPTH INJECTION

(75) Inventors: Dustin Thompson, Santa Rosa, CA (US); Patrick Macaulay, Santa Rosa, CA (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 0 days.

(21) Appl. No.: 13/100,961

(22) Filed: May 4, 2011

(65) Prior Publication Data

US 2012/0109103 A1    May 3, 2012

Related U.S. Application Data

(62) Division of application No. 12/106,839, filed on Apr. 21, 2008, now Pat. No. 7,959,612.

(51) Int. Cl.
  *A61M 5/00* (2006.01)
  *A61M 5/315* (2006.01)
  *B67D 7/70* (2010.01)
  *B65D 88/54* (2006.01)
  *G01F 11/00* (2006.01)

(52) U.S. Cl. ........ 604/500; 604/191; 604/224; 604/227; 222/137; 222/288; 222/390

(58) Field of Classification Search ............ 604/82, 604/187, 191, 224, 207, 209, 211; 222/137, 222/288, 390
See application file for complete search history.

(56) References Cited

U.S. PATENT DOCUMENTS

| | | | |
|---|---|---|---|
| 2,892,457 A | 6/1959 | Sturtz | |
| 3,467,096 A | 9/1969 | Horn | |
| 4,109,653 A * | 8/1978 | Kozam et al. | 604/191 |
| 4,544,369 A | 10/1985 | Skakoon et al. | |
| 4,609,371 A | 9/1986 | Pizzino | |
| 4,610,666 A | 9/1986 | Pizzino | |
| 4,979,942 A * | 12/1990 | Wolf et al. | 604/83 |
| 5,520,658 A | 5/1996 | Holm | |
| 5,584,815 A | 12/1996 | Pawelka et al. | |
| 5,759,171 A | 6/1998 | Coelho et al. | |
| 6,030,357 A | 2/2000 | Daoud et al. | |
| 6,444,228 B1 | 9/2002 | Baugh et al. | |
| 7,604,626 B2 | 10/2009 | McIntosh et al. | |
| 2004/0024353 A1 | 2/2004 | Petersen et al. | |
| 2005/0209564 A1 | 9/2005 | Bonner et al. | |
| 2006/0041242 A1 | 2/2006 | Stypulkowski | |
| 2006/0116646 A1 | 6/2006 | Weiss | |
| 2007/0005020 A1 | 1/2007 | Laveault | |
| 2007/0014784 A1 | 1/2007 | Nayak et al. | |
| 2007/0197954 A1 | 8/2007 | Keenan | |

* cited by examiner

*Primary Examiner* — Kevin C Sirmons
*Assistant Examiner* — William Carpenter

(57) ABSTRACT

Devices and methods for simultaneous injection or delivery of two or more substances from separate syringes. The syringes are loaded into a device that has a handle and a screw driven mechanism for simultaneously depressing the plungers of the syringes. The user grasps the handle and positions the device. Thereafter, the screw mechanism is used to simultaneously advance the plungers of the syringes thereby simultaneously expelling the substances from the syringes.

23 Claims, 4 Drawing Sheets

DEVICES AND METHODS FOR CONTROLLED-DEPTH INJECTION

RELATED APPLICATION

This patent application is a division of copending U.S. patent application Ser. No. 12/106,839 filed Apr. 21, 2008, the entire disclosure of which is expressly incorporated herein by reference.

FIELD OF THE INVENTION

The present invention relates generally to medical devices and methods and more particularly to devices and methods for simultaneous injection or infusion of a plurality of two substances contained in separate syringes.

BACKGROUND

In medicine and surgery, it is sometimes desirable to inject 2 or more drugs or other substances simultaneously, from separate syringes. The prior art has included a number of devices that may generally be used to accomplish this. For example, the prior art has included a number of syringe pumps that may be used to simultaneously expel fluid from 2 or more syringes. Examples of commercially available dual-syringe or multiple-syringe pumps include: the KDS 200 Two-Syringe Infusion Pump, the KDS 101 Two-Syringe Nanoliter Pump, the KDS 220 Multi-Syringe Infusion Pump and the KDS 250 Four-Syringe Nanoliter Infusion Pump (KD Scientific, Inc., Holliston, Mass.); the SP 100i Infusion Pump (World Precision Instruments, Inc., Sarasota, Fla.) and the NE-1600 Multiple Syringe Pump (New Era Pump Systems, Inc., Wantagh, N.Y.).

The prior art has also included dual barrel syringes and apparatus that may be attached to two separate syringes and used to compress the plungers of both syringes simultaneously. For example, U.S. Pat. No. 4,609,371 (Pizzino) describes a dual syringe for either simultaneous or sequential injection of two different injectable liquids. The syringe includes two barrels, each having a plunger for the injection of liquid, and a manually operable three-position rotary valve which controls the filling of the syringe and the outflow of liquid from the syringe. The three positions of the valve permit liquid to be dispensed either from the first barrel only, the second barrel only, or both barrels simultaneously.

Also, U.S. Pat. No. 4,610,666 (Pizzino) describes a syringe having two or more barrels for injection of two or more liquids into a patient in predetermined sequence. The syringe includes a valve, either a slide valve or a rotary valve, which places the barrels one at a time in predetermined sequence in communication in the needle of the syringe. Preferably the syringe is pre-filled with the desired injectable liquids and the valve is preset so that the barrel containing the first liquid to be dispensed is in communication in the needle.

Additionally, United States Patent Application Publication No. 2006/0116646 (Weiss) describes bi-inoculator dual syringe clip of the invention is a unique piece of equipment that is a lightweight, convenient, sterile, and easy to use device that clips two existing syringes together which allows two inoculations to be combined into one step without having to combine the antibodies. The bi-inoculator dual syringe clip comprises a first and second half having at least a first and second pair of curved portions separated by a first and second spacer member. A hinged portion connects the first and second halves together such that the halves can be folded together causing the first pair of curved portions to mate with the second pair of curved portions to form a pair of tubular holding members capable of holding a syringe therein. The bi-inoculator dual syringe clip of the invention improves the method of administering inoculations tremendously and also improves patient care as well as reduces trauma.

Also, United States Patent Application Publication No. 2007/0005020 (Laveault) describes a dual syringe adapter for attachment to a pair of side-by-side syringes includes three interconnected portions. A first portion is configured so as to snap onto a plunger head portion of each syringe so as to connect the pair of syringes and maintain plunger movement in unison. A second portion of the adapter is configured so as to snap onto a syringe body of each syringe to help maintain the connection of the two syringes. The third interconnected portion is positioned between the first and second portions and when connected prevents relative movement of the plungers into the syringe bodies. Weakened sections allow the connecting portion to be severed from the first and second portions thereby allowing plunger movement into the syringe bodies. Once severed, the connecting portion is secured to syringe tips for dispensing a mixed composition.

One procedure currently under development wherein it is desirable to simultaneously inject a plurality of substances involves the deposition of platelet gel (PG) within an infarcted area of myocardium to improve myocardial function and/or to prevent deleterious ventricular remodeling following myocardial infarction or other injury to the myocardium. In this therapy, a platelet-containing component (e.g., platelet rich plasma (PRP)) is injected simultaneously with a thrombin-containing component (e.g., a thrombin solution) such that the platelet-containing component and the thrombin-containing component become mixed in situ (or within the lumen of a needle immediately before entering the myocardium). Such simultaneous injection and in situ mixing of the platelet-containing component and the thrombin-containing component results in the formation of PG, which causes the desired therapeutic effect. More specifically, the PG forms when active substances contained in the platelet-containing component (e.g., fibrinogen) are activated by thrombin contained in the thrombin-containing component. Autologous PRP can be obtained from the subject's own blood, thereby significantly reducing the risk of adverse reactions or infection. When autologous PRP is used as the platelet-containing component, the resultant PG is referred to as autologous platelet gel (APG). The addition of thrombin to platelet-containing plasma products such as PRP is described in detail in U.S. Pat. No. 6,444,228 and United States Patent Application Publication Nos. 2007/0014784, 2006/0041242 and 2005/209564, the disclosures of each such patent and patent application being expressly incorporated herein by reference. Since it is difficult to pass PG or APG through the lumen of a needle, it is desirable to inject the platelet-containing component and the thrombin-containing component such that they become mixed immediately prior to, during or after injection through the needle. Additionally, injecting the platelet-containing component and the thrombin-containing component separately or immediately after mixing may allow the infusate to distribute to a greater area before fully gelling into the PG or PG, thereby possibly enhancing the effect of this therapy. Multiple component injectors that are suitable for simultaneous injection of PRP and thrombin solution are described in U.S. patent application Ser. No. 11/969,094, the disclosure of which is also expressly incorporated herein by reference. U.S. patent application Ser. No. 11/969,094 describes a multiple component injector device that uses 2 primary injector syringes and two larger reservoir syringes. The plungers of the two primary syringes are compressed simultaneously in increments to effect repetitive injection of aliquots of the PRP and thrombin solution into the myocardium. When the contents of the primary syringes have been depleted, if it is desired to continue the injection process, the user must refill the primary syringes from the reservoir syringes. This refilling process can require the user to manipulate valves on stopcocks, draw the desired amounts of material from the reservoir syringes into the primary syringes, return the stopcock valves to their original positions and then proceed with further injections of the materials into the myocardium. Control over the volume of each injection and the volume of each refill are dependent on the operator's ability to precisely move the syringe plungers while carefully observing graduated markings on the syringe(s).

There remains a need for the development of new devices and methods for precisely controlled simultaneous injection from two or more syringes while allowing for easy syringe exchange when desired.

SUMMARY OF THE INVENTION

The present invention provides new devices and methods for simultaneous expulsion of fluid from two or more syringes at a controlled rate and/or in controlled increments. In the devices of the present invention, the injection syringes may be pre-loaded with the desired substances and, when the injection syringes become empty, they may be easily replaced.

In accordance with the invention, there is provided a device for simultaneously delivering substances from a plurality of syringes. Such device generally comprises a handle, a syringe barrel supporting structure attached to the handle and constructed to support the barrels of at least first and second syringes, a syringe plunger driving assembly engageable with the plungers of said at least first and second syringes and a screw mechanism useable to advance the syringe plunger driving assembly in a distal direction, thereby causing the syringe plungers to expel substances from the syringes. In some embodiments, the handle may comprise a grip portion (e.g., a pistol grip) sized to be grasped by a single human hand. The syringe plunger driving assembly may, in some embodiments, comprise a yoke assembly that has an upper member and a lower member moveable between an open position and a closed position. The syringe plungers may be inserted into the yoke assembly while it is in its open position and will be retained within the yoke assembly when it is in its closed position. In some embodiments, the screw mechanism may comprise a rotatable shaft having threads which engage corresponding threads on the plunger driving assembly and knob for controlling rotation of the shaft.

Further in accordance with the invention, there is provided a method for simultaneous delivery of first and second substances. Such method generally comprises the steps of (A) providing a device that comprises; a handle; a syringe barrel supporting structure attached to the handle and constructed to support the barrels of first and second syringes; a syringe plunger driving assembly engageable with the plungers of the first and second syringes and a screw mechanism useable to advance the syringe plunger driving assembly in a distal direction; (B) providing a first syringe having a barrel, a plunger and a quantity of the first substance within the barrel; (C) providing a second syringe having a barrel, a plunger and a quantity of the second substance within the barrel; (D) loading a first syringe and second syringe into the device such that the barrel supporting structure supports the barrels of the first and second syringes and the plunger driving assembly engages the plungers of the first and second syringes; (E) grasping the handle and positioning the device and (E) using the screw mechanism to simultaneously advance the syringe plunger driving assembly in a distal direction, thereby causing the syringe plungers to simultaneously expel the first and second substances from the first and second syringes. In some embodiments of the method, the device provided in Step A may include a manifold that is attached to the syringes and a delivery cannula that is attached to the manifold so that substances from the syringes flow through the manifold and then through common lumen or separate lumens of the cannula. The delivery cannula may comprise a sharp tipped needle or a blunt tipped cannula. When a sharp tipped needle is used, the needle may be inserted into tissue (e.g., an organ, muscle, tumor, etc) and the combined substances may then be injected into the tissue through the cannula.

Further or alternative elements, aspects, objects and advantages of the present invention will be understood by those of skill in the art upon studying of the accompanying drawings and reading of the detailed description and examples set forth below.

DETAILED DESCRIPTION AND EXAMPLES

Figure 1:
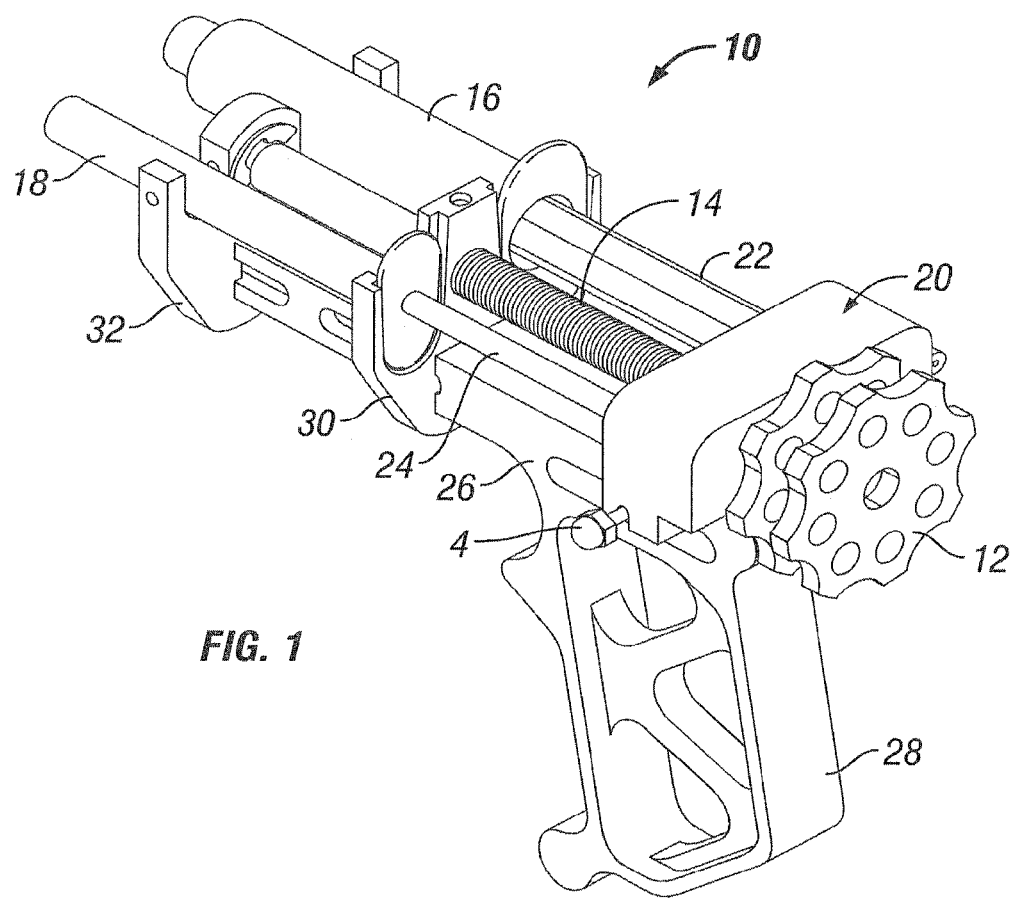
FIG. 1 is a rear perspective view of one embodiment of a dual syringe injector device of the present invention.

The following detailed description, the accompanying drawings are intended to describe some, but not necessarily all, examples or embodiments of the invention. The contents of this detailed description and accompanying drawings do not limit the scope of the invention in any way.

Described in detail below is one non-limiting example of a dual syringe injector device 10 that is useable for simultaneous injection of substances from first syringe 16 and a second syringe 18. This device 10 may be used for various procedures wherein two substances are to be injected simultaneously, including but not limited to the injection of a platelet-containing component and thrombin-containing component to accomplish in situ formation of PG or APG as described above. This device 10 avoids the need for refilling of the injector syringes by providing for easy syringe exchange. Also, this device 10 provides for delivery of precise injectate volumes by employing a lead screw mechanism whereby the operator turns a knob 12 which causes rotation of a threaded screw shaft 14 which in-turn advances a plunger driving yoke assembly 20 which depresses the syringe plungers 22, 24. This mechanism allows the lateral motion of the syringe plungers to be controlled and tuned based on the pitch of the screw thread, thereby providing for delivery of desired injectate volumes at controlled rates with greater precision than can normally be accomplished by hand depression of the syringe plungers 22, 24 while visually observing graduation markings on the barrels of the syringes 16, 18.

In the particular example shown, the device 10 includes a handle member 26 having a pistol-like hand grip 28. A syringe barrel supporting structure comprising a proximal syringe holding cradle 30 and a distal syringe holding cradle 32 at spaced-apart locations is attached to a distal portion of the handle member 26, as shown. A non-threaded distal portion 34 of screw shaft 14 is inserted through center apertures 36 and 38 of syringe holding yokes 30 and 32 and the distal end 40 of the screw shaft 14 is rotatably connected to the distal syringe holding yoke 32 by way of shaft retaining rings 44 or any other suitable rotational connection well known in the art, such as a bearing assembly. The proximal end of the screw shaft 14 is non-rotatably connected to the knob 12.

The plunger driving assembly 20 comprises an upper member 42 that is attached by way of a hinge 43 to a lower member 46. Right and left plunger-receiving depressions 48 and 50, as well opposite sides of a screw shaft engaging bore 52, are formed in opposing locations in the upper and lower members 42, 46, as shown. The lower half of screw shaft engaging bore 52 formed within lower member 46 is not threaded, thereby allowing the threaded portion 35 of screw shaft 14 to easily slide back and forth through the lower half of the screw shaft engaging bore 52. The upper half of screw shaft engaging bore 52 formed within upper member 42 is threaded so as to engage corresponding threads on the threaded portion 35 of screw shaft 14.

Figure 2A:
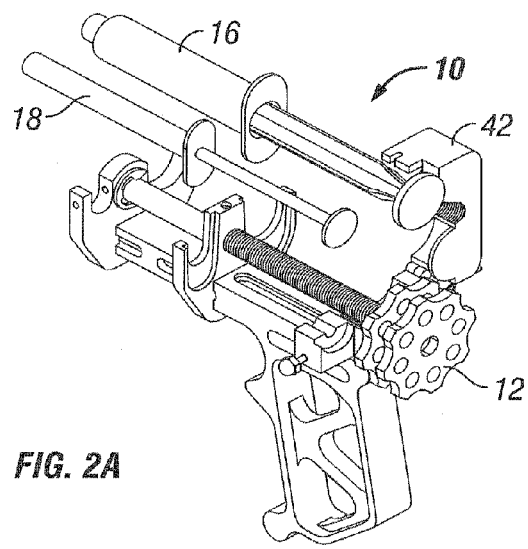
FIGS. 2A through 2C show steps in a method for loading two syringes into the dual syringe injector device of FIG. 1.
Figure 2B:
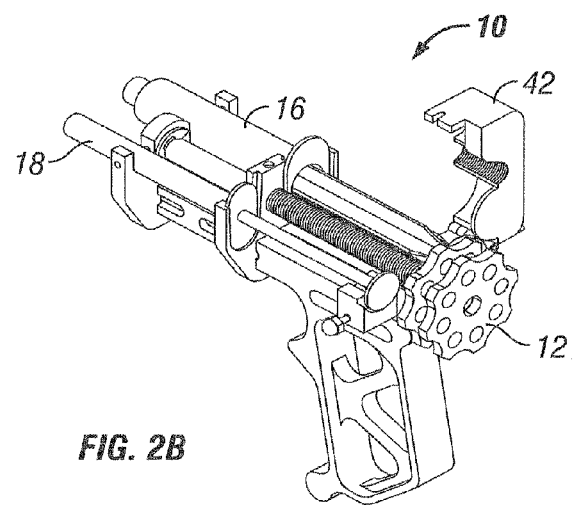
Figure 2C:
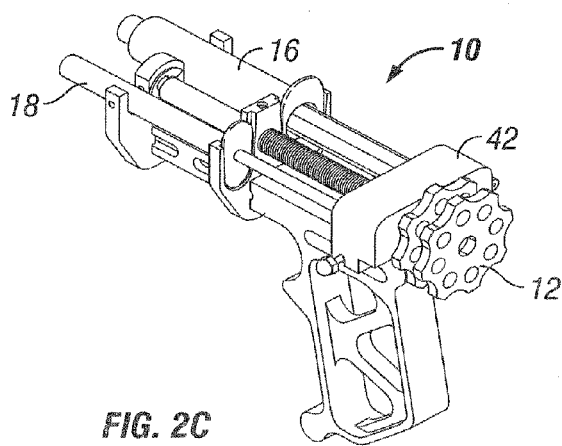
Figure 3:
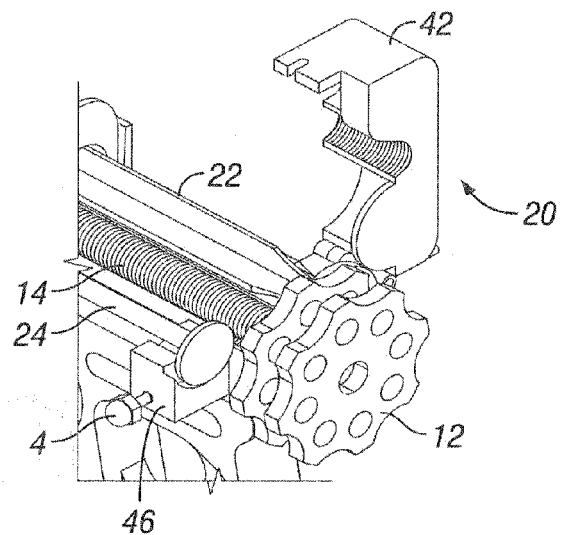
FIG. 3 is a partial rear perspective view of the dual syringe injector device of FIG. 1 wherein in an open configuration to permit loading of syringes into the device.

In operation, the syringes 16, 18 may be pre-filled with the desired substances. When it is desired to load the syringes 16, 18 into the device 10, the top portion 42 of plunger driving yoke assembly 20 will be pivoted about hinge 43 in "clam shell" fashion to an open position, as shown in FIGS. 2A, 2B and 3. With the yoke assembly 20 in such open position, the upper threaded portion of the shaft engaging bore 52 is disengaged with the threaded portion of the screw 35, thereby allowing the user to pull the yoke assembly 20 to the proximal position. The barrels of the syringes 16, 18 may then be dropped into cradles 30, 32 and thumb flanges 56, 58 on the proximal ends of the syringe plungers 22, 24 may be inserted into the plunger-receiving depressions 48, 50 on lower portion 46. Thereafter, as seen in FIG. 2B, the top portion 42 of the may then be pivoted downwardly about hinge 43 to a closed position and spring loaded latch 4 may engage the top portion 42 to latch the plunger driving yoke assembly 20 in its closed configuration, as seen in FIG. 2C. In this manner, the thumb flanges 56, 58 on the proximal ends of the syringe plungers 22, 24 are firmly clamped and held between opposite sides of the plunger-receiving depressions 48, 50 and the threads on the proximal threaded portion 35 of screw shaft 14 are in engagement with the corresponding threads on the upper half of screw shaft engaging bore 52.

The distal male luer connectors 60, 62 of syringes 16, 18 may be connected to separate tubes or delivery cannulas (e.g., sharp needles or blunt cannulas) or, alternatively, may be connected to a manifold that will channel the substances expelled from the syringes 16, 18 into a delivery cannula (e.g., a sharp needle or blunt cannula) having either; a) a single lumen within which the substances re combined or separate side-by-side or b) concentric lumens which will keep the substances separate from each other until they have exited the distal end of such cannula. Examples of on such manifold, as well as biaxial and coaxial delivery cannulas, are described in the above-incorporated U.S. patent application Ser. No. 11/969,094. The delivery cannula(s) is/are then inserted into bodily tissue or otherwise positioned at the location at which the user intends to deposit the substances or mixture of the substances. Thereafter, the user will rotate the knob 12 in the clockwise direction by an amount that corresponds to the volume of injectate to be delivered. Such clockwise rotation of knob 12 causes the screw mechanism to advance the syringe plungers 22, 24 as described above, thereby expelling the desired volume of each substance from each syringe 16, 18 and through whatever down-line manifold(s) or cannula(s) to which the syringes 16, 18 may be connected.

Figure 4:
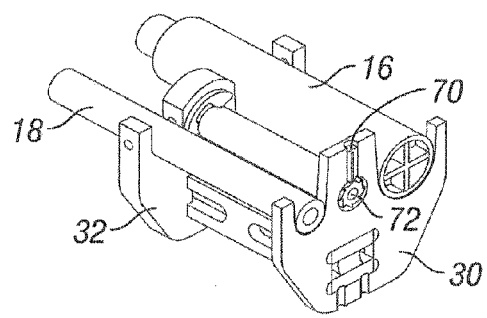
FIG. 4 is a partial rear perspective view of a distal portion of the device of FIG. 1 having two syringes positioned therein.
Figure 4A:
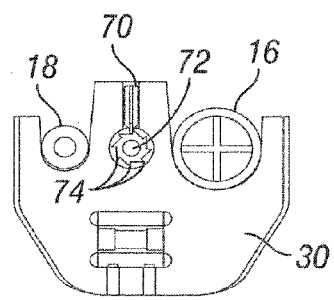
FIG. 4a is a rear end view of the distal portion of the device shown in FIG. 4.
Figure 5:
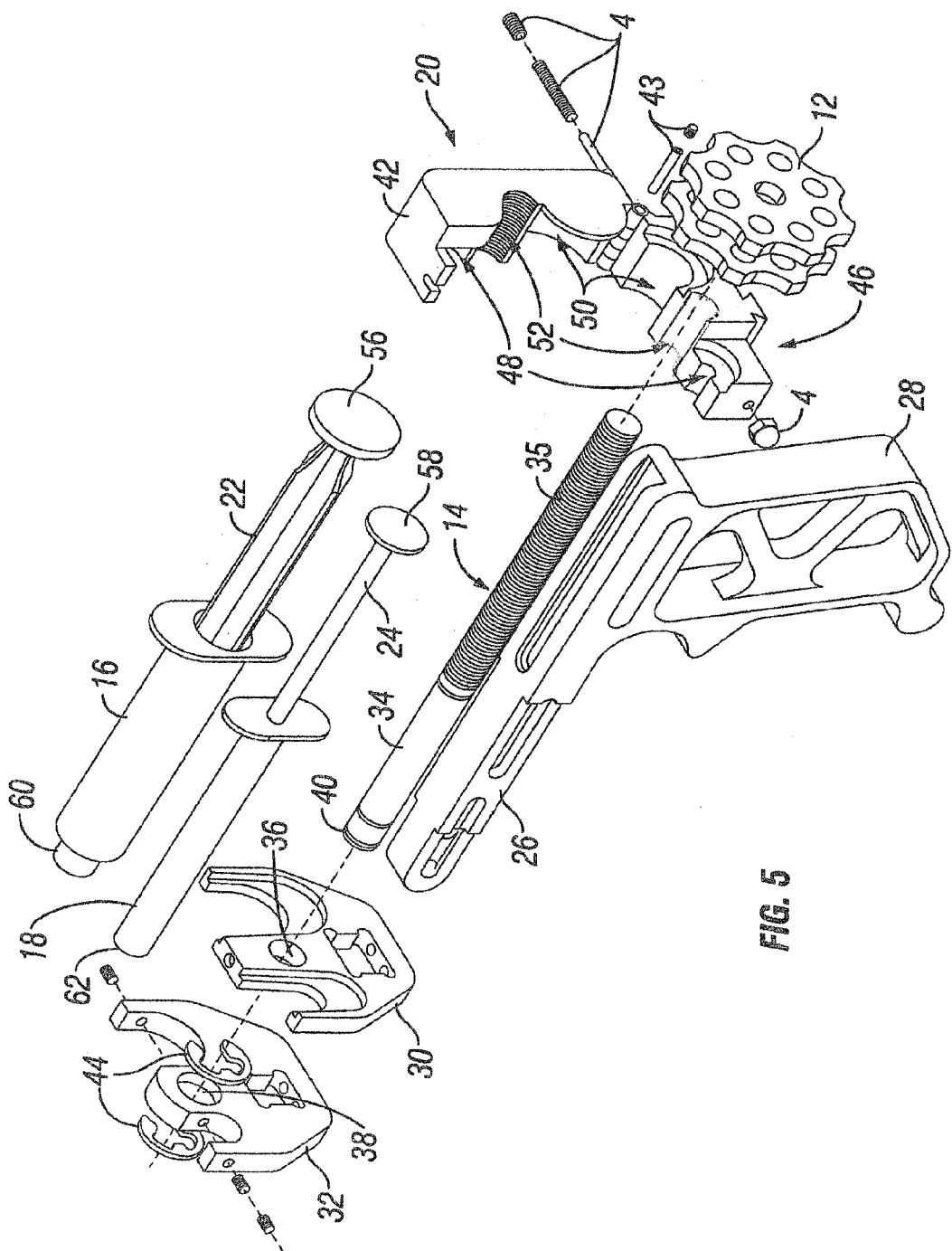
FIG. 5 is an exploded view of the device of FIG. 1.

Graduated or incremental markings which correlate to the volume of injectate delivered may be provided on the device 10 and/or on the syringes 16, 18 to enable the user to gage the distance to which the knob 12 must be rotated to deliver the desired volume of injectate. Additionally or alternatively, as shown in FIGS. 4 and 4A, the screw shaft 14 may be associated with a ratchet mechanism which can be used to gage the volume of injectate delivered (e.g., each "click" of the ratchet indicates the delivery of a particular volume of injectate) and/or to prevent unintentional reverse (e.g., counterclockwise) rotation of the screw shaft 14. In this embodiment, a spring loaded pawl 70 (which may comprise a spring-loaded ball-nose set screw) rides on the teeth 74 of gearwheel 72. As the pawl 70 snaps over the trailing side of each tooth 74 on the gearwheel 72, an audible sound or other signal may be provided to notify the operator that another incremental volume (e.g., 0.1 cc) of injectate has been delivered. Also, the teeth 74 may be shaped such that the pawl 70 slides over the teeth 74 when the knob 12 and screw shaft 14 are rotated in the desired direction (e.g., the direction which causes the intended expulsion of the substances from syringes 16, 18) but catches on the teeth to prevent the knob 12 and screw shaft 14 from being rotated in the opposite direction. Alternatively, the device 10 may be constructed so that the operator may manually disengage the pawl 70 from gearwheel 72 if and when there is some reason the turn the knob 12 and screw shaft 14 in the opposite direction, such as an event when there is a desire to pull the syringe plungers 22, 24 in the proximal direction to aspirate fluid into the syringes 16, 18.

Although the above-described device 120 uses a screw mechanism for advancement of the syringe plungers, those skilled in the art will recognize that various other mechanisms could alternatively be used to advance the syringe plungers 22, 24. One such mechanism could be a ratcheting pawl against a toothed rack. The toothed rack would be attached to the syringe pistons by a common yoke connected to the syringe pistons. In this design, a trigger (otherwise a lever) could be depressed causing the ratcheting pawl to push the toothed rack a specified distance. Furthermore, the specified distance could correspond to a certain dispensed volume from both syringes.

Advantages of at least some embodiments of the above-described invention of some of the prior art devices include a) ergonomic advantages because the operator is required to hold only one device 10, b) reduced eye-strain in embodiments that do not require the operator to read graduations on the syringes in order to meter out the desired injectate volumes, c) decreased force required to advance syringe plungers, d) the ability to deliver more injections per syringe and e) precise control of volume delivery.

The delivery ratio if the substances may be controlled by altering the relative sizes of the syringes 16, 18 and syringe holding cradles 30, 32 and the plunger receiving depressions 48, 50 may vary in size to accommodate different syringe size combinations. For example, where a 1 to 1 delivery ratio is desired (i.e., 1 cc of component A for each 1 cc of Component B), the syringes 16, 18 may be of the same size. Where a different delivery ratio is desired, the syringes 16, 18 may differ in size. In the particular example shown, the right syringe 16 is a 10 cc syringe and the left syringe 18 is a 1 cc syringe, thereby giving rise to a 10 to 1 delivery ratio, as will be suitable for therapeutic PG or APG injection into the myocardium where 10 parts platelet rich plasma (PRP) is mixed with 1 part thrombin solution. When delivering such PG or APG therapy, the site of injection may be within or near an area of impaired myocardial function and the PG or APG may have the effect of improving myocardial function and/or preventing deleterious or maladaptive ventricular remodeling.

It is to be appreciated, however, that this invention has many uses in addition to delivering PG or APG therapy. For example, the device 10 may be used to deliver various other two component therapies such as two-component tissue adhesives and sealants (e.g., Tisseel VH™ Fibrin Sealant, available commercially from Baxter Healthcare Corporation, Deerfield, Ill.), two-component tissue bulking agents, fillers or polymeric materials (e.g., hydrogels) that may be formed or expanded in situ for various therapeutic or cosmetic applications (e.g., tissue bulking, filling or expanding) and various prodrug+activator combinations.

Additionally, it is to be appreciated that, although the specific embodiment shown in the drawings is constructed to utilize only two syringes, various other embodiments of this invention may be configured for simultaneous injection from 3 or more syringes.

It is to be further appreciated that the invention has been described hereabove with reference to certain examples or embodiments of the invention but that various additions, deletions, alterations and modifications may be made to those examples and embodiments without departing from the intended spirit and scope of the invention. For example, any element or attribute of one embodiment or example may be incorporated into or used with another embodiment or example, unless to do so would render the embodiment or example unsuitable for its intended use. Also, where the steps of a method or process are described, listed or claimed in a particular order, such steps may be performed in any other order unless to do so would render the embodiment or example not novel, obvious to a person of ordinary skill in the relevant art or unsuitable for its intended use. All reasonable additions, deletions, modifications and alterations are to be considered equivalents of the described examples and embodiments and are to be included within the scope of the following claims.

What is claimed is:

1. A method for simultaneous delivery of first and second substances, said method comprising the steps of:
   (A) obtaining or providing a device that comprises; a handle; a syringe barrel supporting structure attached to the handle and constructed to support the barrels of first and second syringes; a syringe plunger driving assembly engageable with the plungers of the first and second syringes and a screw mechanism comprising a threaded rotatable shaft, wherein the syringe plunger driving assembly comprises an upper member and a lower member, at least one of said upper and lower members being moveable relative to the other to cause the syringe plunger driving assembly to transition back and forth between i) an open configuration wherein the plungers of the syringes may be inserted into the syringe plunger driving assembly and the threads of the threaded rotatable shaft do not engage any corresponding threads on the syringe plunger driving assembly and ii) a closed position wherein the plungers of the syringes are engaged by the syringe plunger driving assembly and threads of the threaded rotatable shaft are engaged with corresponding threads on the syringe plunger driving assembly such that subsequent rotation of the shaft will drive the syringe plunger driving assembly in the distal direction thereby causing the plungers of the syringes to advance further into the barrels of the syringes;
   (B) loading a quantity of the first substance within the barrel of a first syringe having a barrel and a plunger;
   (C) loading a quantity of the second substance within the barrel of a second syringe having a barrel and a plunger;
   (D) with the syringe plunger driving assembly in its open configuration, placing the first syringe and second syringes into the device such that the barrel supporting structure supports the barrels of the first and second syringes and the plungers of the first and second syringes are positioned within the syringe plunger driving assembly and, thereafter, transitioning the syringe plunger driving assembly to its closed configuration;
   (E) grasping the handle and positioning the device; and
   (F) causing the threaded rotatable shaft to rotate, thereby advancing the syringe plunger driving assembly in a distal direction, thereby advancing the syringe plungers to within the barrels of the first and second syringes, thereby simultaneously expelling the first and second substances from the first and second syringes.

2. A method according to claim 1 wherein the device provided in Step A further comprises a manifold that is attachable to the syringes and a delivery cannula that is attachable to the manifold and wherein the method further comprises the steps of:
   attaching the manifold to the syringes; and
   attaching the delivery cannula to the manifold.

3. A method according to claim 2 wherein the delivery cannula comprises a needle and wherein positioning the device in Step E of the method comprises inserting the needle into tissue.

4. A method according to claim 3 wherein the needle is inserted into myocardial tissue.

5. A method according to claim 1 wherein the first substance contains platelets and the second substance contains thrombin and wherein the platelets and thrombin combine either within the device or in situ after exiting the needle to form platelet gel.

6. A method according to claim 1 wherein the first substance comprises platelet rich plasma and the second substance comprises thrombin solution and wherein the syringes are sized to deliver approximately 10 parts of platelet rich plasma per 1 part thrombin solution.

7. A method according to claim 1 wherein the handle comprises a grip portion sized to be grasped by a single human hand and wherein Step E comprises grasping the handle with a single hand.

8. A method according to claim 1 wherein the syringe barrel supporting structure comprises at least first and second syringe barrel supporting cradles at spaced-apart locations and wherein Step D comprises placing the first and second syringes such that the barrels of the first and second syringes are received within said cradles.

9. A method according to claim 1 wherein the syringe plunger driving assembly comprises a hinged yoke assembly.

10. A method according to claim 1 wherein the screw mechanism further comprises a knob is attached to the proximal end of the threaded rotatable shaft and wherein Step F comprises using said knob to facilitate rotation of the shaft.

11. A method according to claim 1 wherein one semi-cylindrical portion of a rotatable shaft receiving bore is formed in the upper member and an opposite semi-cylindrical portion of that rotatable shaft receiving bore is formed in the lower member;
   wherein the upper member is moveable between an open position to effect the open configuration of the syringe plunger driving assembly and a closed position to effect the closed configuration of the syringe plunger driving assembly; and wherein the semi-cylindrical portion of the bore formed in the upper member is threaded and the opposite semi-cylindrical portion of the bore formed in the lower member is substantially smooth and devoid of threads.

12. A method according to claim 11 wherein, while the upper member is in its open position, the threads of its semi-cylindrical portion of the shaft receiving bore do not engage the threads on the threaded rotatable shaft and the threaded rotatable shaft is axially slidable through the non-threaded semi-cylindrical portion of the shaft receiving bore formed in the lower member.

13. A method according to claim 12 wherein the upper and lower members additionally have opposing portions of syringe plunger receiving cavities formed therein and, with the upper member in its open position, the plungers of the syringes are insertable into the portions of the plunger receiving cavities formed in the lower member and, thereafter, when the upper member is moved to its closed position, the plungers of the syringes are retained within the plunger receiving cavities such that they may be axially driven by advancement of the syringe plunger driving assembly.

14. A method according to claim 1 wherein the screw mechanism is useable to cause the threaded rotatable shaft to rotate in a rotational direction that causes the syringe plungers to advance in the distal direction but not in an opposite rotational direction that would cause the syringe plungers to retract in the proximal direction.

15. A method according to claim 1 wherein the device further comprises a ratchet mechanism comprising a toothed gearwheel that rotates along with the shaft and a pawl that rides on the toothed gearwheel.

16. A method according to claim 15 wherein the ratchet mechanism incrementally delivers metered volumes of the substances.

17. A method according to claim 15 wherein the ratchet mechanism is constructed to allow the shaft to rotate in a direction that causes the syringe plungers to advance in the distal direction but to deter rotation of the shaft in the opposite direction.

18. A method according to claim 1 wherein the first and second syringes are the same size.

19. A method according to claim 1 wherein the first and second syringes differ in size.

20. A method according to claim 1 wherein the first syringe is loaded with a platelet-containing substance and the second syringe is loaded with a thrombin-containing substance.

21. A method according to claim 20 wherein the platelet containing substance comprises platelet rich plasma or autologous platelet rich plasma.

22. A method according to claim 20 wherein the thrombin containing substance comprises thrombin solution.

23. A method according to claim 20 wherein the syringes are sized to deliver the platelet-containing substance and the thrombin containing substance in a ratio of approximately 10 parts platelet containing substance to 1 part thrombin containing substance.

* * * * *